United States Patent [19]

Matsuura

[11] Patent Number: 5,109,865
[45] Date of Patent: May 5, 1992

[54] METHOD AND APPARATUS FOR EXAMINING OVARY AND DIAGNOSING THE PRESENCE OF PREGNANCY IN MAMMALS

[75] Inventor: Masayuki Matsuura, Hamamatsu, Japan

[73] Assignee: Kabushiki Kaisha Semex Japan, Shizuoka, Japan

[21] Appl. No.: 474,783

[22] PCT Filed: Jul. 27, 1989

[86] PCT No.: PCT/JP89/00749
§ 371 Date: Mar. 28, 1990
§ 102(e) Date: Mar. 28, 1990

[87] PCT Pub. No.: WO90/01304
PCT Pub. Date: Feb. 22, 1990

[30] Foreign Application Priority Data

Jul. 29, 1988 [JP] Japan .................. 63-189922
Jul. 29, 1988 [JP] Japan .................. 63-189923
Feb. 10, 1989 [JP] Japan .................. 1-32344

[51] Int. Cl.⁵ .................................. A61B 10/00
[52] U.S. Cl. .................................. 128/738
[58] Field of Search ............. 128/738, 734, 788, 736

[56] References Cited

U.S. PATENT DOCUMENTS

| | | | |
|---|---|---|---|
| 3,297,020 | 1/1967 | Mathiesen | 128/738 |
| 3,749,089 | 7/1973 | Derr | 128/738 |
| 3,844,276 | 10/1974 | McDougall | 128/738 |
| 4,224,949 | 9/1980 | Scott et al. | 128/738 |
| 4,498,481 | 2/1985 | Lemke | 128/736 |

FOREIGN PATENT DOCUMENTS 2548638 4/1976 Fed. Rep. of Germany ...... 128/738
169444 10/1983 Japan .

OTHER PUBLICATIONS

Medical & Biological Engineering & Computing, vol. 18, No. 1, Jan. 1980, pp. 73-80, D. E. Frances.

Primary Examiner—Max Hindenburg
Attorney, Agent, or Firm—Oliff & Berridge

[57] ABSTRACT

According to the present invention, the types and the stages of the ovarian disorders or the presence of pregnancy may be diagnosed from the results of measured sodium ion concentration on vaginal mucosa and change therein, based on the impedance value between the electrodes 14 and 14 on the vaginal mucosa, while compressing the electrodes 14 and 14 on the vaginal mucosa in mammals.

6 Claims, 7 Drawing Sheets

METHOD AND APPARATUS FOR EXAMINING OVARY AND DIAGNOSING THE PRESENCE OF PREGNANCY IN MAMMALS

TECHNICAL FIELD

The present invention relates to a method for examining ovary and diagnosing the presence of pregnancy in mammals and the apparatus therefor.

BACKGROUND ART

The ovarian disorders in mammals include, for example, follicle growth termination syndrome in cows wherein the follicle stops its growth in an estrous cycle, leading to the suspension of the cycle for several days; delayed ovulation phenomenon wherein ovulation occurs following the phenomenon described above; and its reverse phenomenon such as atresia follicle i.e., closed follicle, induced by atrophic follicle. All of these disorders are diagnosed as follicle growth impairment or ovarian insufficiency.

Alternatively, cows sometimes do not show any estrous cycle for a long period even though they are not pregnant. In these cases, the cows not having been in parity are diagnosed as follicle growth impairment, whereas the cows in parity are diagnosed as atrophic follicle. More severe cases are diagnosed as hypoovarianism or retention syndrome of corpus luteum.

Ovarian cyst is also included in such disorders other than those aforementioned.

Conventionally, the ovarian disorders have been diagnosed by doctors, based on a variety of examination results. In particular, cattle, such as cows, and pigs have been examined through veterinarian's rectal examination as to whether they have such disorders.

On the other hand, the presence or absence of pregnancy in humans has been determined by the results of urea test and ultra-sonography while in cattle, such as cows, and pigs it has been determined by the rectal examination by veterinarians.

However, frequent rectal examination in cows by veterinarians, for example, causes some problems, such as damaged follicle and catarrhal rectum induced by imposed pressure thereon.

Additionally, if hormone therapy is performed under some instinct of veterinarians at diagnosis, it can cause some adverse problem such as the incidence of corpus luteum cyst and follicle cyst. Similar problems have been suggested in humans besides the cattle such as cows.

As an additional problem, it is impossible to carry out rectal examination in large-sized Holstein cows and overfatted beef cattle, because they are overweight and superfatted, so that underlying follicle disorders or the presence of pregnancy cannot be diagnosed in them.

Particularly in cows, the uterus is enclosed by the pelvis so that it cannot be examined and diagnosed by ultrasonography. In humans, there is certain anxiety regarding the adverse effects of ultrasonography on a fetus, as well as disadvantages of the urea test, such as being a complex, time-consuming and costly procedure.

The present invention has been achieved to solve the conventional problems heretofore mentioned. The object of the present invention is to provide a method for examining an ovary and an apparatus therefor, which realize the diagnosis in mammalian ovary in a safe and secure manner.

Another object of the present invention is to provide a method for diagnosing the presence or absence of pregnancy and the apparatus therefor, which realize safe, rapid and low-cost diagnostic technique of pregnancy in mammals.

Further object of the present invention is to provide a method for examining an ovary and diagnosing the presence or absence of pregnancy and the apparatus therefor, which can realize the examination and diagnosis of ovarian disorders and pregnancy even in cases such as cows, which cannot be given rectal examination.

DISCLOSURE OF THE INVENTION

The present invention may accomplish the above objects by diagnosing severeness of follicle insufficiency in a manner such that in the process where the sodium ion concentration on the vaginal mucosa in mammals in an estrous cycle change decreasingly from a high-level unfertilizability band over time, follicle insufficiency is diagnosed to be severe when the change in the sodium ion concentration stops at a low-level unfertilizability band; diagnosed to be moderate when the change stops at a high-level intermediate band; or diagnosed to be mild when the change stops at a low-level intermediate band, on the basis of the following assumptions; the sodium ion concentration on the mammalian vaginal mucosa substantially equal to that in water or mammalian saliva is designated as the minimum value just before ovulation and the concentration substantially equal to that in mammalian blood is designated the maximum value during the stage where no ovulation occurs (non-ovulation stage); the range between the maximum and the minimum values is divided into at least the unfertilizability band corresponding to the sodium concentration on the vaginal mucosa during the non-ovulation stage, the ovulation band corresponding to that during the stage just before ovulation having a high probability of establishing pregnancy, and the intermediate band corresponding to that at the intermediate stage between the unfertilizability and ovulation bands; the unfertilizability band is divided into at least a high-level and a low level unfertilizability bands, depending on the level of the sodium ion concentration, whereas the intermediate band is divided into at least a high-level and a low level intermediate bands, depending on the level of the sodium ion concentration.

The present invention may accomplish the above objects by an apparatus for examining a mammalian ovary composed of a sodium ion concentration detecting means for detecting the sodium ion concentration on mammalian vaginal mucosa and a judgment indicating means for indicating one of a low-level unfertilizability band, a high-level intermediate band and a low-level intermediate band, where the change in the sodium ion concentration stops in the process where the sodium ion concentration detected by the sodium ion concentration detecting means changes decreasingly from a high-level unfertilizability band over time, on a basis of the following assumptions; the sodium ion concentration on the mammalian vaginal mucosa substantially equal to that in water or mammalian saliva is designated the minimum value just before ovulation and the concentration substantially equal to that in mammalian blood is designated the maximum value during the stage where no ovulation occurs (non-ovulation stage); the range between the maximum and the minimum values is divided into at least the unfertilizability band corresponding to the sodium ion concentration on the vaginal mucosa during the non-ovulation stage, the ovulation band corresponding to that during the stage just before ovulation having a high probability of establishing pregnancy, and the intermediate band corresponding to that at the intermediate stage between the unfertilizability and ovulation bands; the unfertilizability band is divided into at least high-level and low level unfertilizability bands, depending on the level of the sodium ion concentration, whereas the intermediate band is divided into at least high-level and low-level intermediate bands, depending on the level of the sodium ion concentration.

The present invention may accomplish the above objects by an apparatus for examining mammalian ovary composed of a sodium ion concentration detecting means comprising a detector to be inserted into mammalian vagina, a plurality of electrodes arranged at the positions in the detector where they may be contacted with the vaginal mucosa, a voltage generating means for applying a voltage across the plurality of electrodes and an impedance detector for detecting an impedance across the electrodes; and a judgment indicating means indicating one of a low-level unfertilizability band, high-level and low-level intermediate bands, where the change in the equivalent impedance value on vaginal mucosa detected by the impedance detector stop in the process where the equivalent impedance value changes increasingly over time from the minimum value, on a basis of the following assumptions that the equivalent impedance on the mammalian vaginal mucosa substantially equal to that in water or saliva from the mammals is designated as the maximum value just before ovulation and the impedance substantially equal to that in mammalian blood is designated the minimum value in the non-ovulation stage; the value between the minimum and the maximum values is represented in correspondence with one of the high-level and low-level unfertilizability bands and the high-level and the low-level intermediate bands.

The present invention has accomplished the above objects by diagnosing ovarian disorders in a manner such that a mammal in a long absence of an estrous cycle and not pregnant and with a sodium ion concentration on vaginal mucosa at a high-level unfertilizability band is diagnosed as atrophic ovary, severe ovarian growth impairment, hypoovarianism or retention syndrome of corpus luteum; such mammal with the sodium ion concentration on vaginal mucosa at a low-level unfertilizability band is diagnosed as moderate ovarian growth impairment, hypoovarianism or retention syndrome of corpus luteum; such mammal with the sodium ion concentration on vaginal mucosa at a high-level intermediate band is diagnosed as mild ovarian growth impairment, hypoovarianism or retention syndrome of corpus luteum, on the basis of the following assumptions; a sodium ion concentration on the mammalian vaginal mucosa substantially equal to that in water or mammalian saliva is designated the minimum value just before ovulation and a concentration substantially equal to that in mammalian blood is designated the maximum value during the stage where no ovulation occurs (non-ovulation stage); the range between the maximum and the minimum values is divided into at least the unfertilizability band corresponding to the sodium ion concentration on the vaginal mucosa during the non-ovulation stage, the ovulation band corresponding to that during the stage just before ovulation having a high probability of establishing pregnancy, and the intermediate band corresponding to that at the intermediate stage between the unfertilizability and ovulation bands; the unfertilizability band is divided into at least high-level and low-level unfertilizability bands, depending on the level of the sodium ion concentration, whereas the intermediate band is divided into at least high-level and low-level intermediate bands, depending on the level of the sodium ion concentration.

The present invention may accomplish the above objects by being comprised of a sodium ion detecting means for detecting the sodium ion concentration on mammalian vaginal mucosa and a judgment indicating means indicating the value of the sodium ion concentration in mammals in a long absence of an estrous cycle and not in pregnancy, which is detected by the sodium ion concentration detecting means and which is between a low-level unfertilizability band and a high-level intermediate band, in the process where the sodium ion concentration changes decreasingly over time from the high-level unfertilizability band, on a basis of the following assumptions; the sodium ion concentration on the mammalian vaginal mucosa substantially equal to that in water or mammalian saliva is designated the minimum value just before ovulation and the concentration substantially equal to that in mammalian blood is designated the maximum value during the stage where no ovulation occurs (non-ovulation stage); the range between the maximum and the minimum values is divided into at least the unfertilizability band corresponding to the sodium ion concentration on the vaginal mucosa during the non-ovulation stage, the ovulation band corresponding to the stage just before having a high probability of establishing pregnancy, and the intermediate band corresponding to that at the intermediate stage between the unfertilizability and ovulation bands; the unfertilizability band is divided into at least high-level and low level unfertilizability bands, depending on the level of the sodium ion concentration, whereas the intermediate band is divided into at least high-level and low-level intermediate band, depending on the level of the sodium ion concentration.

The present invention may accomplish the above objects by an apparatus for examining mammalian ovary composed of a sodium ion concentration detecting means comprising a detector to be inserted into mammalian vagina, a plurality of electrodes arranged at the positions in the detector where they may be contacted with the vaginal mucosa, a voltage generating means for applying a voltage across the plurality of electrodes and an impedance detector for detecting an impedance across the electrodes; and a judgment indicating means indicating the value between a minimum and a maximum in correspondence with high-level and low-level unfertilizability bands and high-level and low-level intermediate bands, on a basis of the following assumptions that the equivalent impedance on the mammalian vaginal mucosa substantially equal to that in water or saliva from the mammals is designated the maximum value just before ovulation and the impedance substantially equal to that in mammalian blood is designated the minimum value in the non-ovulation stage; the value between the minimum and the maximum values is represented in correspondence with one of the high-level and low-level unfertilizability bands and the high-level and the low-level intermediate bands.

The present invention has accomplished the above objects by diagnosing follicle cyst in mammals when the sodium ion concentration on mammalian vaginal mucosa changes between the unfertilizability band and the ovulation band, at a cycle of several seconds or less, on a basis of the following assumptions; the sodium ion concentration on the mammalian vaginal mucosa substantially equal to that in water or mammalian saliva is designated the minimum value just before ovulation and the concentration substantially equal to that in mammalian blood is designated the maximum and minimum value in the non-ovulation stage; the range between the maximum and minimum values is divided into at least the unfertilizability band corresponding to the sodium ion concentration on vaginal mucosa in the unfertilizability stage, the ovulation band corresponding to that in the stage just before ovulation having a high probability of establishing pregnancy, and the intermediate band corresponding to that at the intermediate stage between the unfertilizability and ovulation bands.

The present invention may accomplish the above objects, by being composed of a sodium ion concentration detecting means for detecting the sodium ion concentration on mammalian vaginal mucosa and a judgment indicating means indicating possible periodic change between an unfertilizability band and an ovulation band, on the basis of the following assumptions; the sodium ion concentration on mammalian vaginal mucosa substantially equal to that in water or saliva from mammals is designated as the minimum value just before ovulation and the sodium ion concentration substantially equal to that in mammalian blood is designated as the maximum value in the non-ovulation stage; the range between the maximum and minimum values is divided into at least the unfertilizability band corresponding to that on the vaginal mucosa at the unfertilizability stage, the ovulation band corresponding to the stage just before ovulation with a high probability of pregnancy and the intermediate band corresponding to the intermediate band between the unfertilizability and the ovulation bands.

The present invention may accomplish the above objects, by composing the apparatus for examining mammalian ovary of a sodium ion concentration detecting means comprising a detector to be inserted into mammalian vagina, a plurality of electrodes arranged at the positions in the detector where they may be contacted with the vaginal mucosa, a voltage generating means for applying a voltage across the plurality of electrodes and an impedance detector for detecting an impedance across the electrodes and a judgment indicating means indicating the equivalent impedance value between a minimum and a maximum values in correspondence with an unfertilizability band, a low-level intermediate band and an ovulation band, on the basis of the following assumptions; the equivalent impedance on the mammalian vaginal mucosa substantially equal to that in water or saliva from the mammals is designated the maximum value just before ovulation and the impedance substantially equal to that in mammalian blood is designated as the minimum value in the non-ovulation stage.

The present invention has accomplished the above objects by diagnosing the presence of pregnancy when the sodium ion concentration on mammalian vaginal mucosa is at a low-level intermediate band, on the basis of the following assumptions; the sodium ion concentration on the mammalian vaginal mucosa substantially equal to that in water or mammalian saliva is designated the minimum value just before ovulation and the concentration substantially equal to that in mammalian blood is designated as the maximum value in the non-ovulation stage; the range between the maximum and the minimum values is divided into at least the unfertilizability band corresponding to the sodium ion concentration on the vaginal mucosa during the non-ovulation stage, the ovulation band corresponding to that during the stage just before ovulation having a high probability of establishing pregnancy, and the intermediate band corresponding to that at the intermediate stage between the unfertilizability and ovulation bands; the unfertilizability band is divided into at least high-level and low-level unfertilizability bands, depending on the level of the sodium ion concentration, whereas the intermediate band is divided into at least high-level and low-level intermediate bands, depending on the level of the sodium ion concentration.

The present invention may accomplish the above objects by being composed of a sodium ion concentration detecting means for detecting the sodium ion concentration on mammalian vaginal mucosa and a judgment indicating means for indicating the low-level intermediate band where the sodium ion concentration detected by the sodium ion concentration detecting means is, on a basis of the following assumptions; the sodium ion concentration on the mammalian vaginal mucosa substantially equal to that in water or mammalian saliva is designated the minimum value just before ovulation and the concentration substantially equal to that in mammalian blood is designated the maximum value in the non-ovulation stage; the range between the maximum and the minimum values is divided into at least the unfertilizability band corresponding to the sodium ion concentration on the vaginal mucosa during the non-ovulation stage, the ovulation band corresponding to that in the stage just before ovulation having a high probability of establishing pregnancy, and the intermediate band corresponding to that at the intermediate stage between the unfertilizability and ovulation bands; the intermediate band is divided into at least high-level and low-level intermediate bands, depending on the level of the sodium ion concentration.

The present invention may accomplish the above objects by an apparatus for examining mammalian ovary composed of a sodium ion concentration detecting means comprising a detector to be inserted into mammalian vagina, a plurality of electrodes arranged at the positions in the detector where they may be contacted with the vaginal mucosa, a voltage generating means for applying a voltage across the plurality of electrodes and an impedance detector for detecting an impedance across the electrodes; and a judgment indicating means indicating the low-level intermediate band where an equivalent impedance value detected by the impedance detecting means is, on a basis of the following assumptions that the equivalent impedance on the mammalian vaginal mucosa substantially equal to that in water or saliva from the mammals is designated the maximum value just before ovulation and the impedance substantially equal to that in mammalian blood is designated the minimum value in the non-ovulation stage; the value between the minimum and the maximum values is represented in correspondence with one of the unfertilizability band, the intermediate band, the low-level intermediate band and the ovulation band.

The present invention is based on the findings by the inventors that the sodium ion concentration on the mammalian mucosa reaches the minimum value in the ovulation stage, the value being equal to that in water, or more accurately in saliva from the mammals, while the sodium ion concentration reaches the maximum value at the non-pregnant and non-ovulation stages, the value being equal to that in mammalian blood.

The present invention is also based on findings that the sodium ion concentration on the vaginal mucosa falls into a specific range between the minimum and the maximum values or demonstrates a specific change, depending on the types and the stage of the ovarian disorders in mammals or the presence or absence of pregnancy.

The present invention may realize examination of an ovary or the presence or absence of pregnancy using a sodium ion concentration on mammalian vaginal mucosa which varies or shows a specific value, depending on the types of ovarian disorders in mammals or the presence of pregnancy.

BEST MODE FOR CARRYING OUT THE INVENTION

Figure 1:
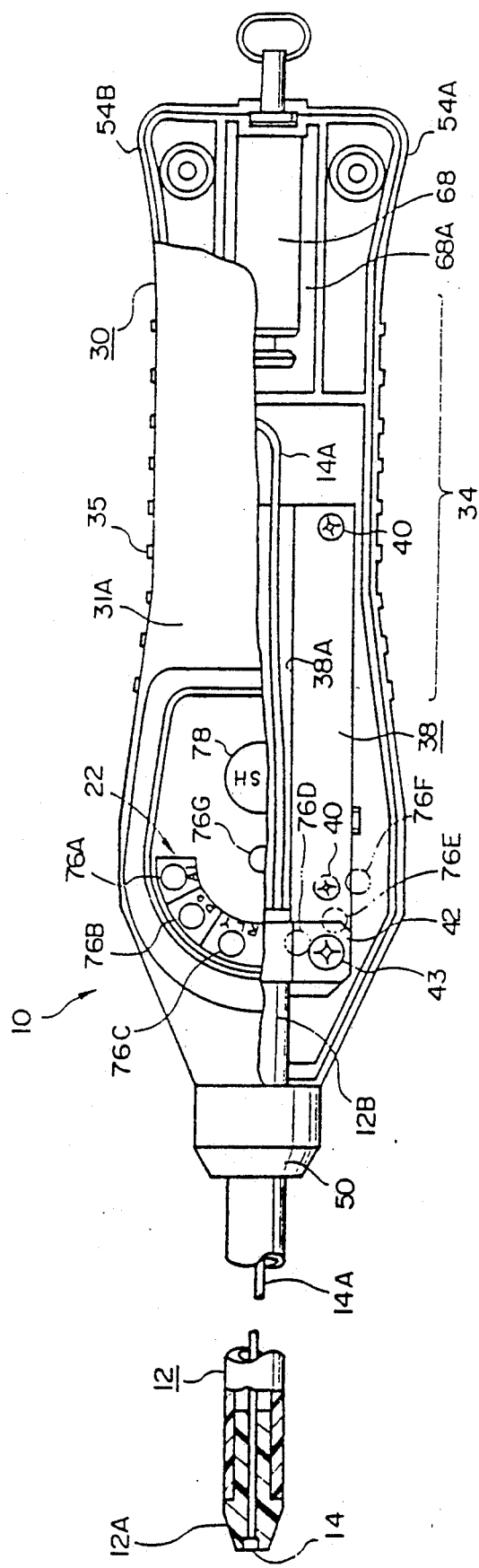
FIG. 1 is a top plan view partly in section for showing a preferred embodiment of an apparatus for examining and diagnosing an ovary and the presence of pregnancy in mammals in accordance with the present invention.

As illustrated in the drawings, one preferred embodiment relates to a fertilizability detecting apparatus 10 for mammals comprising sodium ion concentration detecting means 20 including a bar-like detecting part 12 which can be inserted into a vagina of mammals, a pair of electrodes 14 and 14 arranged at positions in an extremity end 12A of the bar-like detector 12 where they can be contacted with a mucous membrane in the mammals, and voltage generating means 16 for applying a voltage across the pair of electrodes 14 and 14; and a judgment indicating means 24 including a level-judging means 18 for detecting a band selected from the group consisting of 6 bands described below, to which the equivalent impedance value on the vaginal mucosa measured between the electrodes 14 and 14 belongs, on a basis of the following assumptions, the equivalent impedance value on the mammalian vaginal mucosa substantially equal to that in water or subjective mammalian saliva is designated the maximum value just before ovulation and the value substantially equal to that in subjective mammalian blood is designated the minimum value, the maximum and the minimum values and the range between the maximum and the minimum values are assigned to the unfertilizability band corresponding to the sodium ion concentration on the vaginal mucosa in the non-ovulation stage, the ovulation band corresponding to that in the stage just before ovulation having a high probability of establishing pregnancy, and the intermediate band corresponding to that the intermediate stage between the unfertilizability and ovulation bands, each of the unfertilizability band, the intermediate band and the ovulation band is divided into high-level and low-level unfertilizability bands, high-level and low-level intermediate bands, high-level and low-level ovulation bands, respectively, depending on the level of the sodium ion concentration, and indicating means 22 for indicating an impedance value of the vaginal mucous membrane detected by the impedance detecting device 18 in response to this value.

The fertilizability detecting apparatus 10 includes a hollow case 30 for supporting the indicating means 22 in a surface 31A, supporting a base end side 12B of the bar-like detecting part 12 at one longitudinal end 32A and having a gripping part 34 which can be gripped at an intermediate part of a longitudinal direction; and further the base end 12B of the bar-like detecting part 12 is supported by the hollow case 30 at a part where it enters from one end 32A of the hollow case 30 into the hollow case 30.

The hollow case 30 is constructed such that its upper case 30A and its lower case 30B are connected to each other by small screws 36, and then its abutted surface 30 is placed in a plane passing through a central axis of the bar-like detecting part 12.

The bar-like detecting part 12 is made of hollow pipe-like synthetic resin except for the extremity end 12A, which is supported in the hollow case 30 with its central axis being displaced toward the rear surface 31B in respect to a central axis of the hollow case 30.

Figure 3:
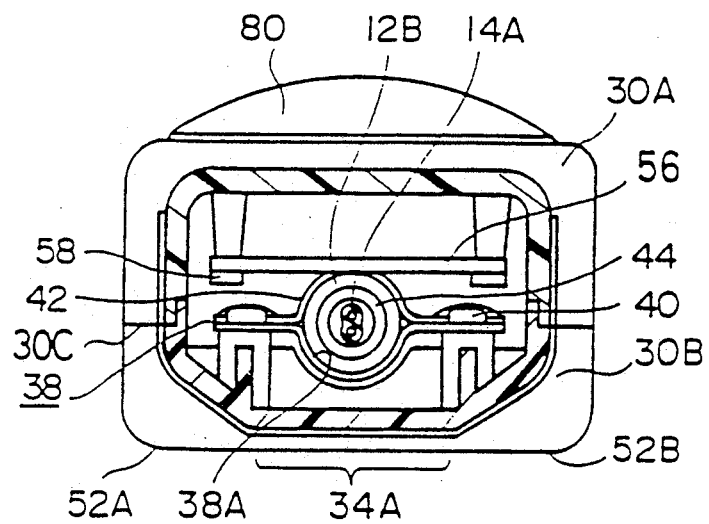
FIGS. 3 to 5 are enlarged sectional views taken along a line III—III to a line V—V of FIG. 2.

As shown in FIG. 3, the rear surface 31B of the hollow case 30 is made such that both corners in a width direction are chamferred in a range of the gripping part 34 so as to form the narrow part 34A. That is, the hollow case 30 is made such that a shape of a section crossing at a right angle with the bar-like detecting part 12 at the gripping part 34 forms a modified pentagonal shape.

Therefore, the bar-like detecting part 12 is arranged such that its central axis line is adjacent to the inner surface of the narrow width part 34A within the hollow case 30.

At the gripping part 34 of the hollow case 30 are arranged a plurality of circumferential projections 35 at its outer circumferential surface in a longitudinal direction in side-by-side relation except at the surface 31A.

The part of the rear surface 31B in the hollow case 30, that is, the surface of the lower case 30B which is adjacent to both ends in a longitudinal direction of the gripping part 34 is, as viewed from an axial direction of the hollow case 30, formed with each of a pair of projections 52A, 52B and 54A and 54B projected toward both sides of the narrow width part 34A.

Figure 4:
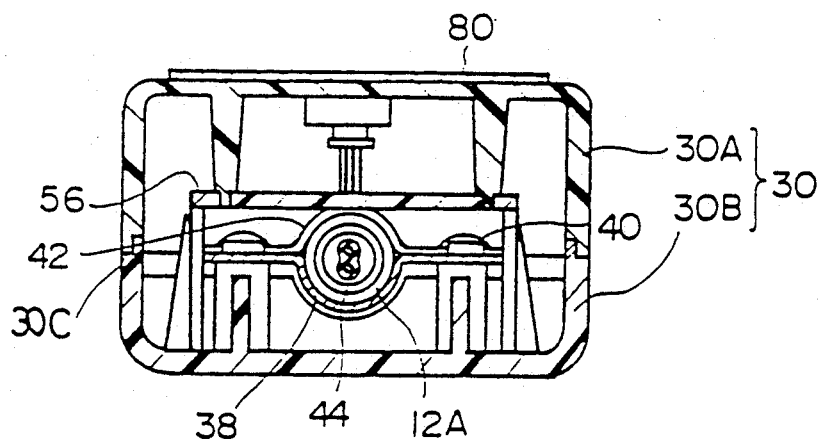
Figure 5:
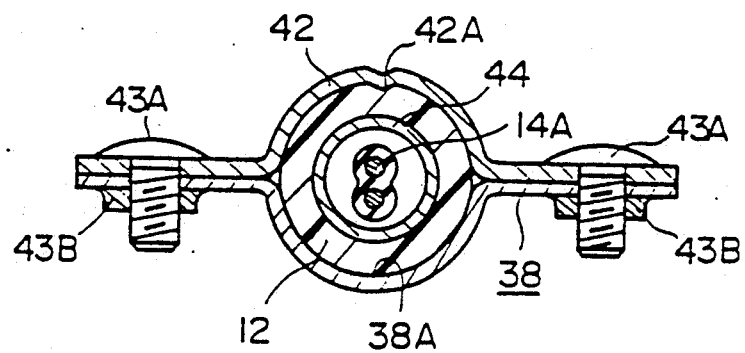

As illustrated in FIGS. 3 and 4, these projections 52A to 54B are projected in parallel with the surface 31A of the hollow case 30 in such a way as their outer shapes become a substantial rectangular shape as viewed from its longitudinal direction, thereby, for example, they prevent the detecting device 10 from falling when the detecting device 10 is placed on a table.

The projections 52A and 52B may constitute a hook for an operator's hands when the bar-like detecting part 12 of the fertilizability detecting device 10 is inserted into a vagina of cows, pigs and the like, and the opposed projections 54A and 54B are constructed to form a hook for the operator's hands when the bar-like detecting part 12 is pulled out of the vagina.

Within the hollow case 30, a supporting bracket 38 is, at its longitudinal intermediate part, fastened and fixed to the lower case 30B by small screws 40.

This supporting bracket 38 is formed with an upward-directed semi-circular concave part 38A as shown in the figure.

A radius of a circular part of this concave part 38A is substantially the same as that of the base end 12B in the bar-like detecting part 12.

The base end 12B of the bar-like detecting part 12 enters from one end 32A in the hollow case 30 into the hollow case 30 and is fastened and fixed to the supporting bracket 38 with a fixing bracket 42 while being fitted to a concave part 38A of the supporting bracket 38.

Reference symbols 43A and 43B in the figure denote a screw and a welded nut for fastening and fixing the fixing bracket 42 to the supporting bracket 38, respectively.

The inner surface of the fixing bracket 42 is formed with a rotation prohibiting projection 42A engaged with an outer circumference of the base end 12B of the bar-like detecting part 12 so as to constitute a rotation prohibiting element for the bar-like detecting part 12 when the fixing bracket 42 is fixed to the supporting bracket 38.

One end 32A in the hollow case 30 is formed with semi-slit male threaded portions 45A and 45B which become a cylindrical shape when they are combined to the upper case 30A and the lower case 30B. Inner sides of these male threaded portions 45A and 45B are formed with semi-arcular grooves 46A and 46B through which the base end 12B of the bar-like detecting part 12 can be inserted.

As shown in the figure, a reinforcing pipe 44 is inserted into the base end 12B fixed between the supporting bracket 38 and the fixed bracket 42.

A length of this reinforcing pipe 44 is set such that when it is inserted into the base end 12B, it may be extended from the position of the fixed bracket 42 to the extremity end positions of the male threaded portions 45A and 45B.

Reference numeral 48 in the figure denotes an O-ring for use in forming a water-proof seal between the extremity ends of the male threaded portions 45A and 45B and an outer periphery of the bar-like detecting part 12. This O-ring 48 is fastened and fixed to the extremity end positions of the male threaded portions 45A and 45B by nuts 50 threadably engaging with the male threaded portions 45A and 45B, respectively. The nuts 50 integrally fasten the upper case 30A and the lower case 30B to each other.

Figure 2:
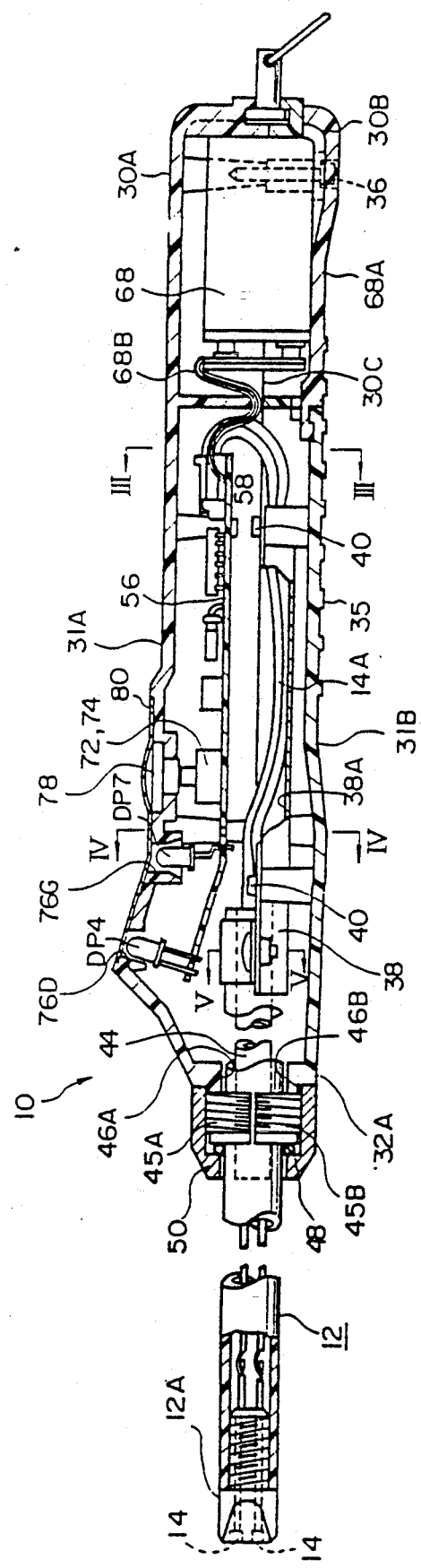
FIG. 2 is a sectional view for showing the preferred embodiment of this invention.

In FIG. 2, within the hollow case 30 is arranged a board 56 spaced apart from and substantially in parallel with it at an upper position of the supporting bracket 38.

This board 56 is fastened and fixed to the upper case 30A with screws 58 so as to support the voltage generating means 16 and the impedance detecting device 18. The indicating means 22 is supported at the upper case 30 through this board 56.

Figure 6:
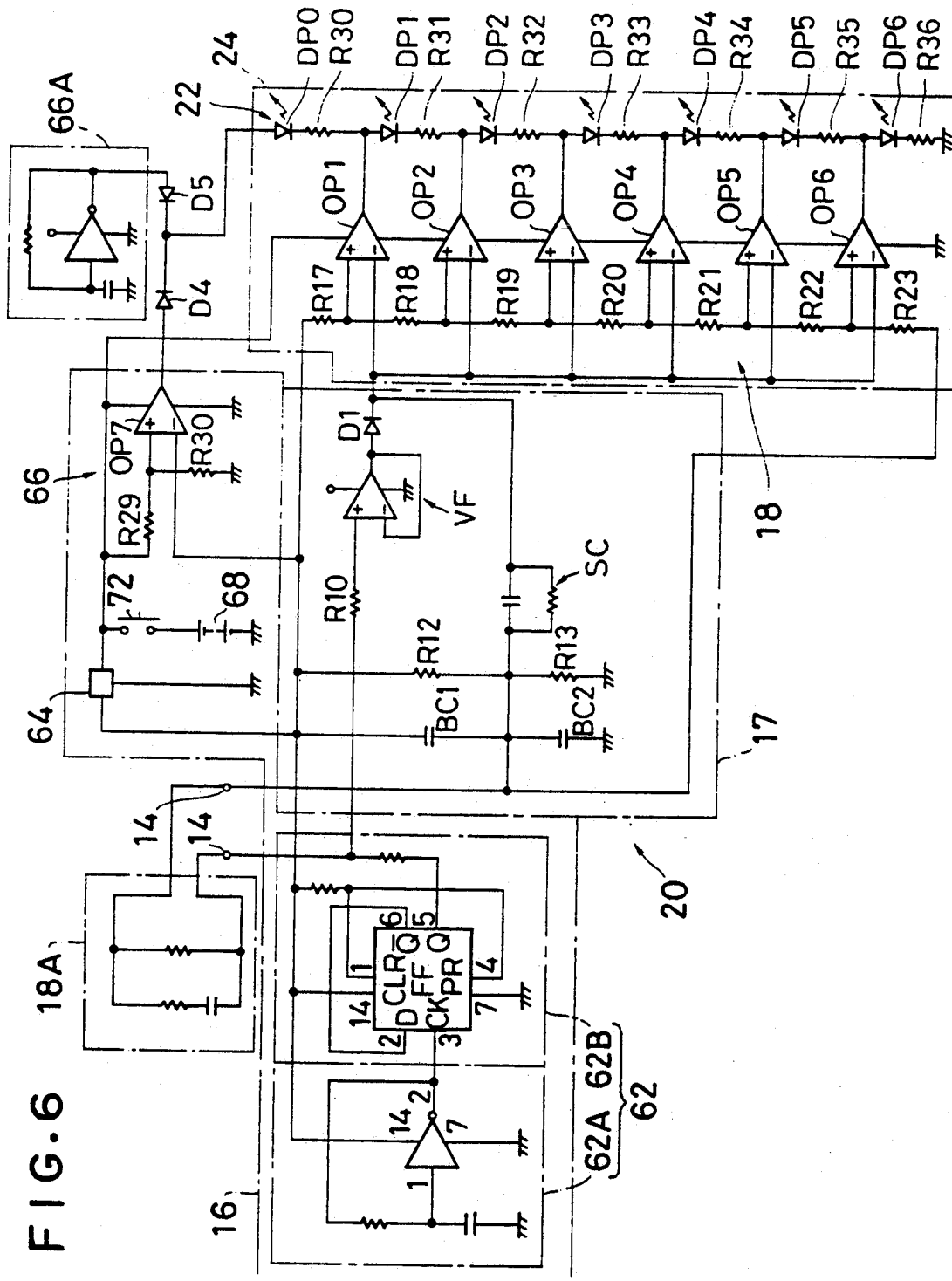
FIG. 6 is an electrical circuit diagram for showing an electrical component part in the preferred embodiment of this invention.
Figure 7:
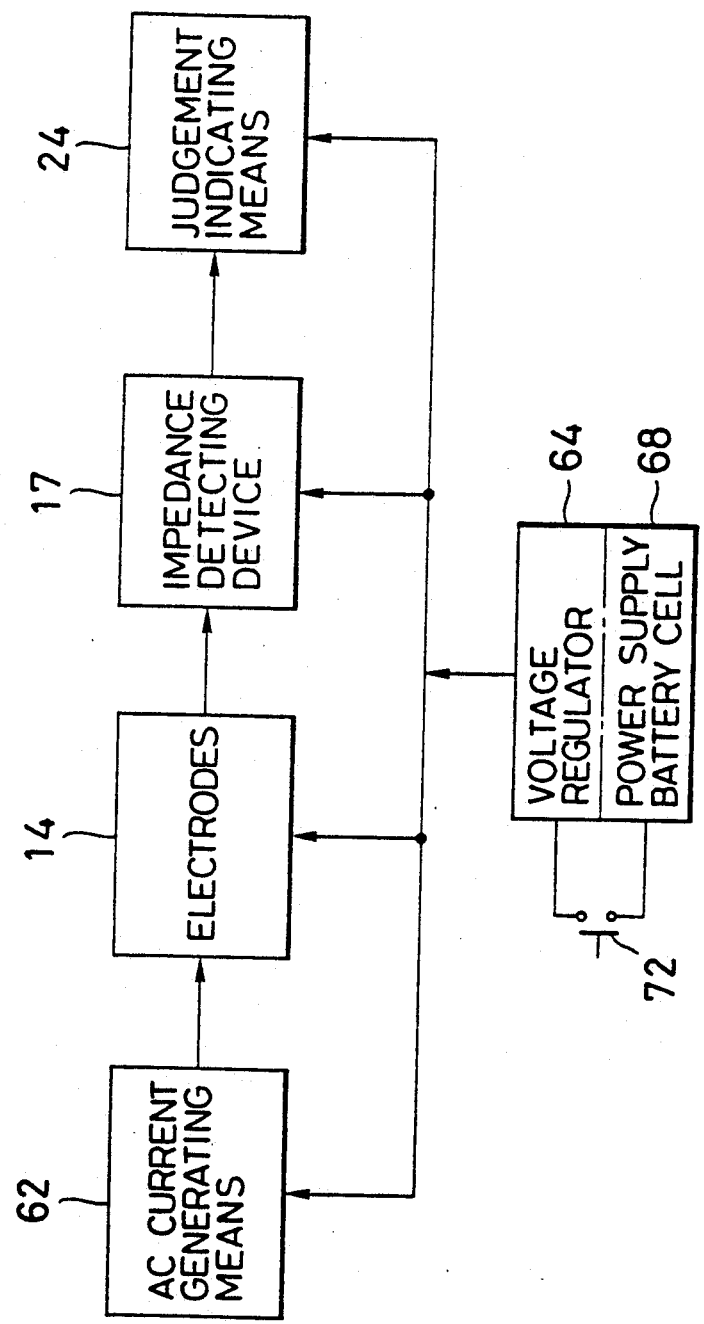
FIG. 7 is a block diagram of this invention.

As illustrated in FIG. 6, the voltage generating means 16 is provided with an AC current generating means 62, a voltage regulator 64 and a voltage comparator device 66.

The AC current generating means 62 is constructed by a square wave form oscillation circuit 62A and ½ frequency divider circuit 62B.

The square wave oscillation circuit 62A is provided with a Schmidt circuit and the ½ frequency divider circuit 62B may divide a pulse outputted by the square wave oscillation circuit 62A by ½ to form a stable square wave.

The voltage regulator 64 includes an invertor circuit for dropping a power supply voltage supplied from a power supply battery cell 68 to a required voltage.

The impedance detecting device 18 is provided with a plurality of calculation amplifiers OP1 to OP6 for use in detecting a level of an impedance of the detected part (vaginal mucous membrane) by AC current applied to the electrodes 14 and 14. The indicating means 22 may indicate each of the levels judged by the impedance level detector 18 by the light emitting diodes DP1 to DP6 in response to each of the levels. The indicating means 22 is provided with a light emitting diode DP0 for use in checking a power supply voltage. In FIG. 6, reference numeral 18A indicates an equivalent circuit for the vaginal mucous membrane acting as the detected part.

The embodiment will be described in more detail. The impedance detector device 18 is provided with resistors R17 to R23 for dividing a voltage inputted from the voltage regulator 64 in order to discriminate a level of the impedance in reference to a voltage signal level outputted from the electrodes 14 and 14 through a resistor R10, a voltage follower VF and a diode D1, and further with calculation amplifiers OP1 to OP6 for use in comparing each of the divided voltages with the voltage signal. To the negative side of the diode D1 is connected a characteristic element of a smoothing circuit SC for use in stabilizing an input voltage signal for each of the calculation amplifiers OP1 to OP6. This smoothing circuit SC is applied with a voltage of the voltage regulator 64 divided by the voltage divider resistors R12 and R13.

Reference symbols BC1 and BC2 in the figure denote a bypass capacitor for these voltage dividing resistors R12 and R13.

The voltage comparator device 66 is used for checking (diagnosing) a decreased voltage of the power supply cell 68 and this is operated by turning on the operation switch 72. The operation switch 72 may also act as an operation switch for operating the impedance detector 18.

The voltage comparator 66 is provided with resistors 29 and 30 and a calculation amplifier OP7 for use in comparing a voltage divided by the resistors 29 and 30 with an output voltage of a voltage regulator 64 in order to diagnose a voltage of the power supply battery cell 68 inputted through the operating switch 72, and this comparator may output a signal to the indicating means 22 through the diode D4 when the voltage is more than a specified value as a result of comparison and diagnosis.

Reference symbols R30 to R36 shown in the figure indicate a resistor for use in dividing the voltage applied to each of the light emitting diodes DP0 to DP6. Reference symbol 66A denotes a rectangular wave oscillation circuit and its output is connected to an output side of the diode D4 through the diode D5. In case of no output of the diode D4, that is, the output voltage of the power supply battery cell 68 is less than a specified value, this output is impressed to the indicating means 22.

In this case, a sum of the resistances of the voltage dividing resistors R18 to R23 at the impedance detector 18 is set to show a value slightly lower than the impedance value between the electrodes 14 and 14 in the water. For example, in case of pigs, a body temperature is normally 38.5° C., so that the electrodes 14 and 14 are immersed in the water of 38.5° C. and then the value is about the impedance value between the electrodes 14 and 14. In this case, this water is human drinking water, for example, tap water, well water or water having an electrical resistance equivalent to these waters. The impedance value in saliva is determined and established in cow's mouth.

The resistance value of the voltage dividing resistor R23 is set substantially equal to an impedance value between the electrodes 14 and 14 in the blood of object mammals.

A sum of resistance values of the voltage dividing resistors R19 to R23 is substantially equal to the impedance value between the electrodes 14 and 14 in the vaginal mucous membrane of the mammals at the time which is suitable for feeding chilled semen into the uterus. That is, the range between the voltage dividing resistors R18 to R23 and the resistors R19 to R23 corresponds to the low-level ovulation band; the range between the voltage dividing resistors R19 to R23 and the resistors R20 to R23 corresponding to the high-level ovulation band.

A sum of the resistance values of the voltage dividing resistors R20 to R23 is substantially equal to an impedance value between the electrodes 14 and 14 at the vaginal mucous membrane of the mammals at the time which is suitable for feeding frozen semen. That is, the range between the voltage dividing resistors R20 to R23 and the resistors R21 to R23 corresponds to the low-level intermediate band; the range between the voltage dividing resistors R21 to R23 and the resistors R22 to R23 corresponds to the high-level intermediate band.

A sum of the resistance values of the voltage dividing resistors R22 and R23 is substantially equal to an impedance value between the electrodes 14 and 14 at the vaginal mucous membrane in case of unfertilizable state at the time of unfertilizable condition of the objective mammals. That is, the range between the voltage dividing resistors R22+R23 and R23 corresponds to the low-level unfertilizability band; the range lower than the voltage of the voltage dividing resistor R23 corresponds to the high-level unfertilizability band.

The power supply battery cell 68 is stored at a right end position of the hollow case 30 as shown in FIGS. 1 and 2. Reference symbol 68A in FIG. 2 denotes a battery cell cover which is removably attached to the lower case 30B.

The power supply battery cell 68 is connected to the board through a lead wire 68B.

To the board 56 is connected a lead wire 14A from the electrodes 14 and 14, respectively. The electrodes 14 and 14 are buried in the extremity end 12A of the bar-like detector 12 and fixed there. The lead wire 14A passes from the electrodes 14 and 14 into the hollow part of the bar-like detector 12 and reaches into the hollow case 30 and from this part it passes through a concave part 38A of the supporting bracket 38 and then further reaches to board 56.

The surface 31A of the hollow case 30 in FIG. 2 is formed with its longitudinal left part being projected in an upward inclined direction. In this figure, six circular windows 76A to 76F are formed in an arcular form under a substantially equal spaced-apart angle. One window 76G is also formed at a central position of the arcular part.

The light emitting diodes DP1 to DP6 in the indicating means 22 are inserted from below in FIG. 2 into the windows 76A to 76F arranged in an arcular form and its emitted light can be confirmed from outside area.

In to the window is also inserted a light emitting diode DP0 from below in FIG. 2 for use in checking a voltage.

Each of these light emitting diode DP0 to DP6 is supported in the board 56.

At the surface 31A of the hollow case 30 are arranged some symbols for indicating the meaning of each of the lighted-up conditions of the light emitting diodes DP1 to DP6 at the positions near six windows 76A to 76F arranged in an arcular form, that is the band-indicating means 22A to 22F displaying the symbols 1 to 6, indicating, respectively, the low-level ovulation band just before ovulation, the high-level ovulation band corresponding to the stage where semen is possibly injected, the high-level intermediate band too early for the above stage, the low-level and high-level unfertilizability bands where injected semen cannot induce fertilization. Furthermore, the symbol P expressing pregnancy is arranged on the downside of the band-indicating means 22C for the low-level intermediate band.

Figure 8:
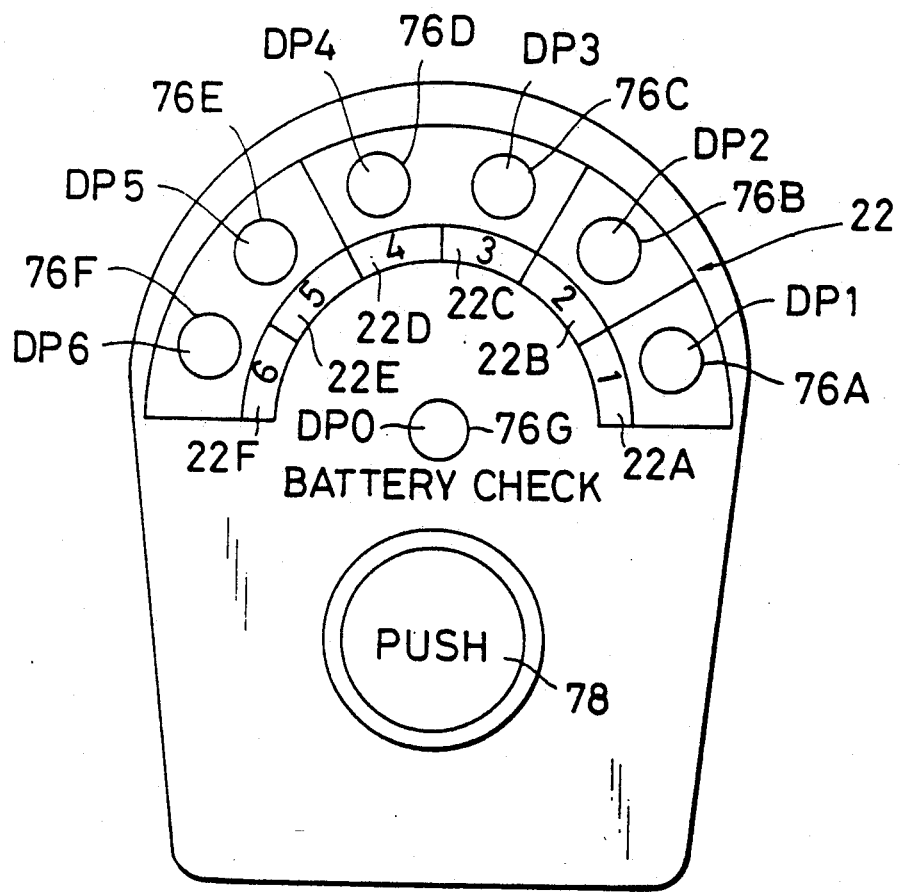
FIG. 8 is a plan view for showing a preferred embodiment of a judgment indicating means and indicated bands thereof.
Figure 9:
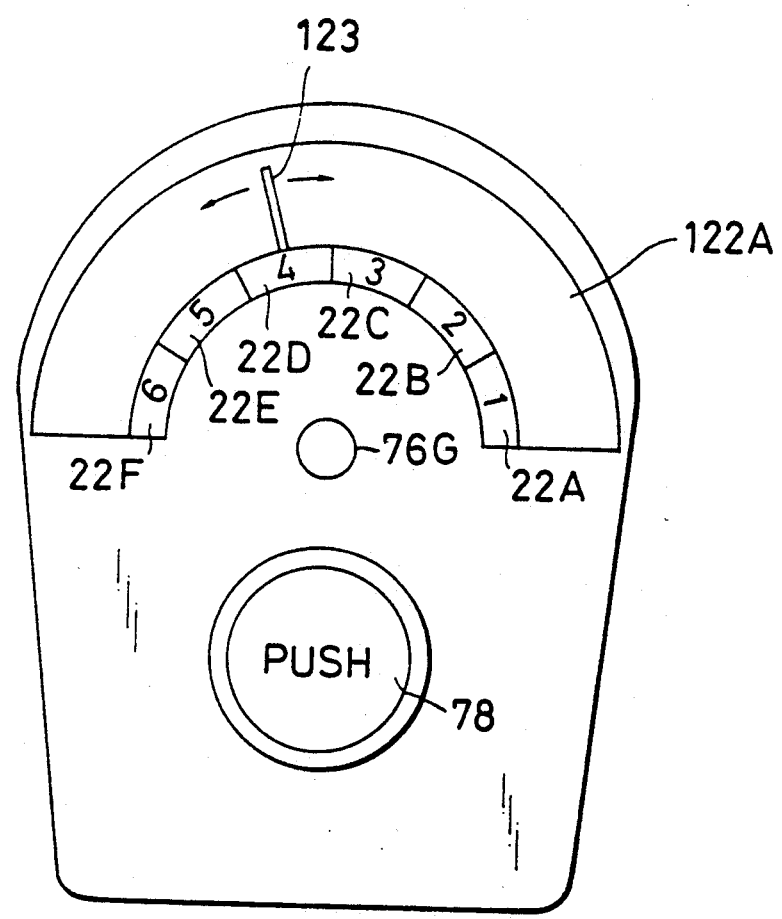
FIG. 9 is a plan view similar to FIG. 8 for showing a second embodiment of the present invention.

At the under position in FIG. 8 a push button 78 is arranged for a light emitting diode DP0 for use in checking the battery cell.

This push button 78 may turn on the operating switch 72. At the upper surfaces of the windows 76A to 76G the push button 78 is attached a thin film 80 of synthetic resin so as to provide a water-proof and protecting action for these windows 76A to 76G and the push button 78. An emitted light from the light emitting diode DP0 to DP6 inserted and held in the windows 76A to 76G can be confirmed from outside through the thin film 80.

In the above-mentioned preferred embodiment, since the base end 12B of the bar-like detector 12 is supported by the hollow case 30 through the supporting bracket 39 and the fixed bracket 42 at a position within the hollow case 30, even if the fertilizability detecting device 10 is dropped in error, for example, and the extremity end of the bar-like detector 12 is struck against a ground or a floor etc., its striking load may not be concentrated at one end 32A of the hollow case 30, but may be dispersed at the supporting bracket 38 and the fixed bracket 42.

Accordingly, one end 32A of the hollow case 30 would be hardly broken as compared with that of the prior art device.

Further, O-ring 48 would be hardly loosened.

In the above-mentioned preferred embodiment, the central axis of the bar-like detector 12 is arranged at a position displaced toward the rear surface 31B within the hollow case 30 and the rear surface 31B is made as the narrow width part 34A with its both ends in its width direction being chamferred within a range of gripper 24, so that there is no useless space within the hollow case 30. Even if the bar-like detector 12 is projected into the hollow case 30, it is possible to avoid a interference with other members, for example, with the board 56.

In the above-mentioned preferred embodiment, since the reinforcing pipe 44 is inserted inside the bar-like detector 12 within a range where the bar-like detector 12 is contacted with the semi-arcular grooves 46A and 46B and the fixed bracket 42, a striking load applied to the bar-like detector 12 can be received without generating any concentrated stress and this load can be dispersed.

Further, in this preferred embodiment, since both sides in a width direction of the rear surface 31B are chamferred within a range of gripper 24 to form the narrow width part 34A, the dead space part is deleted to improve an efficiency of space of the hollow case 30 and at the same time an easy-to-grip feature for the operator is further improved.

The gripper 34 is provided with a plurality of projections 35 in a transversing direction of the device so as to facilitate gripping gripper 24 for the operator and at the same time projections 52A, 52B and 54B across the narrow width part 34A, the operation is easily performed when the fertilizability detector device 10 is inserted into the vagina of the mammals or pulled out of it. In addition, the projections 52A to 54B may act to prevent a fall of the fertilizability detector 10 when the detector is placed on a table, for example.

The procedure for examining ovary and diagnosing the presence of pregnancy is now explained using the apparatus described in the above embodiment.

At first, the bar-like detector 12 is inserted into the vagina.

Then, the electrodes 14 and 14 of the bar-like detector 12 are pushed against the vaginal mucous membrane and the push button 78 is depressed under this condition.

With this arrangement, a voltage generated in response to an impedance value between the electrodes 14 and 14 is inputted to a non-inverting input terminal of each of the calculation amplifiers OP1 to OP6 through diode D1. In turn, to the reversing input terminals of these calculation amplifiers OP1 to OP6 is applied a voltage divided by each of the resistors R17 to R23. So, a voltage value from the vaginal mucous membrane equivalent circuit 18A is compared with a voltage value of each of the calculation amplifiers OP1 to OP6 and a comparison result is inputted to the corresponding light emitting diodes DP1 to DP6. In this case, the voltage inputted to each of the inverting input terminals is applied with its value being increased in a step-wise manner from the calculation amplifiers OP6 toward OP1 in sequence in response to the resistors R23 to R17.

Accordingly, the calculation amplifiers OP6 to OP1 may operate such that one of them outputs a signal selectively in response to a voltage value of the vaginal mucous membrane equivalent circuit 18A.

When the calculation amplifier OP2 may output a value, for example, the output signal passes through the light emitting diode DP2 and the resistor R3 and reaches an earth side of the power supply line in the calculation amplifier OP3. Thus, the light emitting diode DP2 is lit.

As described above, a sum of resistance values of the voltage dividing resistors R18 to R23 is set substantially equal to an impedance value of water or saliva from the mammals, and further, a sum of the resistance values of the voltage dividing resistors R19 to R23 indicates a period when the frozen semen is deposited under a lit condition of the light emitting diode DP1 due to the fact that the impedance value at the vaginal mucous membrane is substantially equal to the value under a condition in which the chilled semen is deposited. Similarly, when the light emitting diode DP2 is lit, it shows a period which is suitable for depositing the chilled semen.

When the impedance value between the electrodes 14 and 14 is larger than the impedance value in the water, any of the calculation amplifiers OP1 to OP6 do not output any signal, so that the light emitting diodes DP1 to DP6 may not be lit.

For example, in case that the electrodes 14 and 14 are not inserted into the vagina of domestic animals, but left in the surrounding atmosphere, the impedance between the electrodes 13 and 14 is higher than the impedance in water or saliva from the mammals.

Under this condition, if the operating switch 72 is turned on, an electric current is flowed to the indicating means 22 through the voltage comparator 66 and the diode D4 and an energization is carried for the earth side of the power supply line of the calculation amplifier OP1 through the light emitting diode DP0 and the resistor R30.

Thus, the light emitting diode DP0 is lit and this indicates that a voltage of the power supply cell 68 is more than the specified value.

In case the voltage of the power supply cell 68 is less than the specified value, the voltage comparator 66 may not output any signal. In turn, since the rectangular wave oscillation circuit 66A outputs a square wave through diode D5, an output signal of the square wave oscillation circuit 66A is outputted to the light emitting diode DP0 and the resistor R30.

Due to this fact, the light emitting diode DP0 may be flashed in response to an output signal from the square wave oscillation circuit 66A so as to indicate that the output voltage of the power supply cell 68 is less than the specified value.

Since a sum of the resistance values of the voltage dividing resistors R21 to R23 is equally set to a maximum value of the impedance value at the vaginal mucous membrane during an unfertilizability period under a non-ovulation condition, when the light emitting diode DP5 or DP6 is lit, it shows that the objective mammals is in an unfertilizability period.

The sum of the resistances of the voltage dividing resistors R21 to R23 is substantially the same as the maximum equivalent impedance on the mammal's vaginal mucous membrane during an unfertilizable period in which ovulation does not occur, so that when the light emitting diode DP5 or DP6 is lit, it shows an unfertilizable period of the objective mammals.

Since the light emitting diode DP5 indicates a high level during an unfertilizable period, and the light emitting diode DP6 indicates a low level impedance value during an unfertilizable period, if the objective mammal is in the mating season, it is possible to judge that the objective mammal approaches the ovulation period or the ovulation is completed. The light emitting diode DP4 and DP3 indicate an unknown period between the fertilizable period and the unfertilizable period, a so-called gray zone.

Since a resistance value of the voltage dividing resistor R23 is set slightly higher than the impedance value in the blood of the objective mammals, when the electrodes 14 and 14 are immersed in the blood of the objective mammals, the light emitting diode DP5 is turned off.

That is, the electrodes 14 and 14 are immersed in blood, it is possible to check a zero level of the ovulation period detector.

According to the actual measurements by the present inventor, the impedance value on the vaginal mucosa of a cow in an estrous cycle increased from the initiation stage of the cycle as the time passed. That is, the sodium ion concentration on the vaginal mucosa decreased as the time passed.

On checking the above findings by a pregnancy diagnosing apparatus 10, the stage progressed from that of the light emitting diode DP6 with a light on to a serial lighting of the diodes DP5, DP4 and DP3.

However, the serial lighting of such diodes breaks down in case of the cows with ovarian insufficiency.

The results of the examination of a great number of cows with ovarian insufficiency showed that the cow might be diagnosed as having severe ovarian insufficiency when the serial lighting of the light emission diodes stops at the light emission diode DP5; moderate ovarian insufficiency when it stops at the light emission diode DP4; mild ovarian insufficiency when it stops at the light emission diode DP3.

These cows with ovarian insufficiency were successfully treated with simultaneous injections each of an ampoule of 1000 IU of serum gonadotrophic hormone and 2000 MU of placental gonadotrophic hormone, when the serial lighting stopped at the light emission diode DP5.

The symptoms in cows wherein the serial lighting stopped at the light emission diode DP4 was greatly improved by the intra-muscular injection of an ampoule of 500 IU of serum gonadotrophic hormone.

The symptom in the case where the lighting stopped at the light emission diode DP4 was improved by the intra-muscular injection of an ampoule of 500 IU of serum gonadotrophic hormone and an ampoule of 1000 MU of placental gonadotrophic hormone.

Alternatively, there were observed cows with negative reaction of pregnancy test and showing no estrous cycle for a long period, wherein the light emission diode DP6, DP5 or DP4 were kept under lighting on checking by a detecting apparatus for ovulation stage.

The present inventors carried out a vast amount of experiments on cows, so that they concluded that the lighting of the light emission diode DP6 indicated the presence of ovarian atrophia, severe ovarian growth impairment, hypoovarianism, or retention syndrome of corpus luteum; that of the diode DP5 indicated the presence of moderate ovarian growth impairment, hypoovarianism, or retention syndrome of corpus luteum.

In the cases described above, the following therapy may be prescribed.

Firstly, an ampoule of 1000 IU of serum gonadotrophic hormone is injected intra-muscularly.

The following therapies Nos. 2 and 3 may be carried out when the attack of estrous cannot be observed 7 to 10 days or more since then.

The case with degeneration similar to small cyst due to the occurrence and suspension of the estrous cycle following the intra-muscular injection is treated again with intra-muscular injection of an ampoule of 1000 IU of serum gonadotrophic hormone. Estrous is induced in this case in a natural manner, usually after about 40 days. If the degeneration should develop into cyst itself, such a symptom may be satisfactorily improved with the injection of placental gonadotrophic hormone of 2000 to 5000 MU and the like.

The therapy No. 2 is performed as follows.

First, serum gonadotrophic hormone 1000 IU 1A and placental gonadotrophic hormone 2000 MU 1A are simultaneously injected.

The case with severe ovarian growth impairment, which cannot have estrous cycle, is treated with the following therapy No. 3.

Firstly, the native-type follicle hormone (estradiol benzoate) is repeatedly injected at a dose of 2.5 ml each for a 7 day interval. In the case of no occurrence of estrous even after 2 to 3 repeated injections, 5.0 ml of the same are again injected at a 10 day interval, several times, until the occurrence of estrous. In the case with corpus luteum cyst, the intra-muscular injection of 6 mg of PG (a preparation of prostaglandine F2) or the infusion of 3 mg of PG into uterus on the side of corpus luteum may be conducted.

The case with a long absence of estrous and not in pregnancy and with the light emission diode DP4 lighting, was diagnosed an mild ovarian growth impairment, hypoovarianism or retention syndrome of corpus luteum.

Such a case is treated with the intra-muscular injection of 2.5 mg of the native-type follicle hormone. An estrous cycle may occur, generally 1 to 3 days after the intra-muscular injection. The following therapy is carried out in the case with no occurrence of estrous cycle 10 days or more after the injection.

The intra-muscular injection of 6 mg of PG (a preparation of prostaglandine F2) or the infusion of 3 mg PG into uterus on the side of corpus luteum was performed. The therapy induced estrous cycles in most of the cows 2 to 3 days later; some showed delayed occurrence of estrous cycle.

The lighting of the light emission diode DP3 may be observed in cows with ovarian growth impairment, hypoovarianism or retention syndrome of corpus luteum at a probability of 2%, based on the results of the experiments on a great number of cows.

Such cows are given the intra-muscular injection of 1.5 to 2.0 mg of the native-type follicle hormone.

As has been described above, the dose of hormone to be used in the therapy of cows with no estrous cycles accompanied by ovarian disorders may be sufficiently adjusted, as needed basis, depending on which an emission light diode may be lighted.

Accordingly, there have been observed some disadvantages regarding the present hormone therapy carried out under some veterinarians' instinct, such as the incidence of corpus luteum cyst and follicle cyst artificially caused by the therapy itself. However, the method for diagnosing ovarian function and the apparatus therefor according to the present invention enables diagnosis and therapy at the same level as the skilled veterinary technician.

The results of the experiments on a great number of cows carried out by the present inventors proposed the confirmation from the impedance values on vaginal mucosa measured by the present apparatus that the lighting of light emission diodes DP1 to 5 frequently changed, at an interval between 1 to several seconds, in cows with ovarian cyst.

Another experiment proposed the findings that the cow showing no estrous cycle and in pregnancy made the light emission diode DP3 into lighting, based on the results of the examination of the sodium ion concentration on the vaginal mucosa therein. The cow at such stage, which was considered in pregnancy for 20 to 40 days after fertilization, showed a pregnancy rate of 98% when the light emission diode DP3 was lighted.

The pregnancy rate reached 100% in the case when the light emission diode DP3 was again lighted in such cow, at the time of rediagnosis using the present apparatus 10 days later.

The initial pregnancy rate of 98% was established because the light emission diode DP3 might have a 2% probability of lighting in the case with mild ovarian growth impairment, hypoovarianism or retention syndrome of corpus luteum.

Such disorders immediately described above never cause the lighting of the light emission diode DP3 again at a reexamination carried out 10 days after the initial lighting of the diode DP3.

Thus, the case with the lighting of the light emission diode DP3 at a first diagnosis and the relighting thereof at the reexamination 10 days later may be considered to have a pregnancy probability of 100%.

Conventionally, the presence of pregnancy in cows, pigs and the like has been determined by rectal examination. Accordingly, it has been impossible to carry out the rectal examination in large-sized Holstein cows and overfatted beef cattle with over-weight and superfatted symptom. Thus, the apparatus of the present invention enables to diagnose the presence of pregnancy even without rectal examination.

In the above-mentioned preferred embodiment, although the value of impedance value between the electrodes 14 and 14 at the vaginal mucous membrane is detected by the impedance detector 18, this invention is not limited to this arrangement, and in brief, the impedance detecting device capable of detecting the impedance value as it is or detecting if this value corresponds to the divided level or not may be applied.

In the above-mentioned preferred embodiment, although the indicating means 22 is constructed by a plurality of light emitting diodes DP1 to DP6, this invention is not limited to this arrangement, but a device capable of properly indicating a value between the maximum value and the minimum value of the impedance at the vaginal mucous membrane may also be applied.

So, the indicating means 22 may be a normal meter and the like which displays the impedance value. In this preferred embodiment, the impedance of the water is applied as the maximum value, the impedance of the blood is applied as the minimum value and a value between these values may be properly divided to input it as it is and may be displayed in the meter.

In the preferred embodiment above, it is possible to make a more accurate detection of the ovulation period and unfertilizability period as compared with that of the above-mentioned preferred embodiment.

In case that a light emitting diode and the like are used, it is not limited to six shown in the preferred embodiment, but 3 or 2 or more than 7 may also be applied.

Although the above-mentioned preferred embodiment may detect an ovulation period with an impedance at the vaginal mucous membrane, this invention is not limited to this arrangement, but in brief, a device capable of detecting a sodium ion concentration at the vaginal mucous membrane directly or indirectly may also be applied.

Accordingly, other means for detecting sodium ion concentration of the vaginal mucous membrane other than the impedance measurement may also be applied.

Although the above-mentioned preferred embodiment may illustrate the way to examine ovary in cows this invention may also be applicable to other mammals (including humans).

CAPABILITY OF EXPLOITATION IN INDUSTRY

The present invention thus constructed as described above, has great use in the accurate examination and precise diagnosis of ovarian disorders and the presence of pregnancy in mammals. Also, the present invention has great effects in diagnosis in cows in which rectal examination cannot be done.

What is claimed is:

1. A method for diagnosing ovarian follicular insufficiency in a mammal comprising:
    measuring the level of sodium ion concentration of the vaginal mucosa of said mammal; and
    comparing the level thus measured with known sodium ion concentration ranges, said ranges being a top range substantially equal to the sodium ion concentration of mammalian blood having a high top end and low top end, a bottom range substantially equal to the sodium ion concentration of mammalian saliva having a high bottom end and a low bottom end, and a range intermediate between said top range and said bottom range having a high intermediate end and a low intermediate end; and
    diagnosing a degree of ovarian follicular insufficiency in an estrous cycle which changes decreasing from the high top end of the top range over time, a sodium ion concentration level corresponding to the low end of the top range being indicative of severe follicular insufficiency, a sodium ion concentration level corresponding to the high end of the range intermediate between the top range and the bottom range being indicative of moderate follicular insufficiency, and a sodium ion concentration level corresponding to the low end of the range intermediate between the top range and the bottom range being indicative of mild follicular insufficiency.

2. A method for diagnosing disease states in an ovary of a non-pregnant mammal in long absence of an estrous cycle comprising:
    measuring the level of the sodium ion concentration of the vaginal mucosa of said mammal;
    comparing the level thus measured with known sodium ion concentration ranges, said ranges being a top range substantially equal to the sodium ion concentration of mammalian blood having a high top end and a low top end, a bottom range substantially equal to the sodium ion concentration of mammalian saliva having a high bottom end and a low bottom end, and a range intermediate between said top range and said bottom range having a high intermediate end and a low intermediate end; and
    diagnosing a degree of ovarian disease states, a sodium ion concentration level corresponding to the high end of the top range being indicative of atrophic ovary, severe ovarian growth impairment, severe hypoovarianism or severe corpus luteum retention syndrome; a sodium ion concentration level corresponding to the low end of the top range being indicative of moderate ovarian growth impairment, moderate hypoovarianism or moderate corpus luteum retention syndrome, and a sodium ion concentration level corresponding to the high end of the range intermediate between said top and said bottom ranges being indicative of mild ovarian growth impairment, mild hypoovarianism or mild corpus luteum retention syndrome.

3. A method for diagnosing follicular cyst in an ovary of a mammal comprising:

measuring the level of the sodium ion concentration of the vaginal mucosa of said mammal;

comparing the level thus measured with known sodium ion concentration ranges, said ranges being a top range substantially equal to the sodium ion concentration of mammalian blood having a high top end and a low top end, a bottom range substantially equal to the sodium ion concentration of mammalian saliva having a high bottom end and a low bottom end, and a range intermediate between said top range and said bottom range having a high intermediate end and a low intermediate end; and diagnosing ovarian follicular cyst, a sodium ion concentration level corresponding to the top range which changes within a time period of several seconds or less to a sodium ion concentration level corresponding to the bottom range being indicative of an ovarian follicular cyst.

4. A method for diagnosing pregnancy in a mammal comprising:

measuring the level of the sodium ion concentration of the vaginal mucosa of said mammal;

comparing the level thus measured with known sodium ion concentration ranges, said ranges being a top range substantially equal to the sodium ion concentration of mammalian blood having a high top end and a low top end, a bottom range substantially equal to the sodium ion concentration of mammalian saliva having a high bottom end and a low bottom end, and a range intermediate between said top range and said bottom range having a high intermediate end and a low intermediate end; and diagnosing pregnancy, a sodium ion concentration level corresponding to the low end of the range intermediate between said top range and said bottom range being indicative of pregnancy.

5. An apparatus for examining a mammalian ovary comprising:

means for measuring sodium ion concentration for detecting a measured sodium ion concentration on the vaginal mucosa of a mammal;

means for comparing said measured sodium ion concentration with a value of sodium ion concentration substantially equal to mammalian saliva, a value of sodium ion concentration substantially equal to mammalian blood, and a value of sodium ion concentration intermediate between said value substantially equal to mammalian saliva and said value substantially equal to mammalian blood;

indicating means for indicating degrees of ovarian follicular insufficiency, degrees of ovarian disease states, follicular cyst, or pregnancy when said measured sodium ion concentration corresponds to a value of sodium ion concentration indicative of said degree of ovarian follicular insufficiency, said degree of ovarian disease state, follicular cyst, or pregnancy.

6. The apparatus according to claim 5, wherein said sodium ion concentration measuring means comprises:

a detecting unit which is inserted into a mammalian vagina;

a plurality of electrodes arranged on the detecting unit for contacting the vaginal mucosa;

a voltage generator for applying voltage across the plurality of electrodes; and an impedance detector for detecting an impedance across the electrodes;

said indicating means indicating a degree of ovarian insufficiency, a degree of ovarian disease state, follicular cyst, or pregnancy when a detected equivalent impedance on the vaginal mucosa detected by said impedance detector corresponds to an equivalent impedance for a degree of ovarian insufficiency, a degree of ovarian disease state, follicular cyst, or pregnancy, on the basis of minimum impedance.

* * * * *